United States Patent [19]
Ott

[11] 4,005,360
[45] Jan. 25, 1977

[54] PROBE WITH BALL BEARING BALL
[76] Inventor: Albert Ott, Sindelfingerstrasse 118, 7032 Sindelfingen 6, Germany
[22] Filed: Dec. 10, 1975
[21] Appl. No.: 639,574
[30] Foreign Application Priority Data
Dec. 14, 1974 Germany .................. 7441607[U]
[52] U.S. Cl. .......................................... 324/34 TK
[51] Int. Cl.² ................. G01R 33/12; G01N 27/72
[58] Field of Search ............. 324/34 R, 34 TK, 52
[56] References Cited
UNITED STATES PATENTS

| 2,249,166 | 7/1941 | Parker et al. | 324/52 |
| 2,507,529 | 5/1950 | Lipson | 324/34 TK |
| 2,625,585 | 1/1953 | Krouse | 324/34 TK |
| 2,627,119 | 2/1953 | Graham | 324/34 TK |
| 2,933,677 | 4/1960 | Lieber | 324/34 TK |

Primary Examiner—Gerard R. Strecker

[57] ABSTRACT

The present invention relates to a probe for measuring the thickness of thin non-ferromagnetic layers on a ferromagnetic base, with a spherical sector consisting of a ground ball bearing ball, with a pin-like fastener connected to the bottom side of the ball bearing ball, with a magnetizable carrier whose side, facing the spherical sector, has an opening for the fastener to be inserted there and which carries a transmission coil.

16 Claims, 4 Drawing Figures

PROBE WITH BALL BEARING BALL

BACKGROUND OF THE INVENTION

Such arrangements are already known in the art, e.g., from DT-GMS (German Utility Patent) No. 7,336,864. Ball bearing balls are inexpensive, friction resistant and highly accurate. Their spherical shape insures that the probe does not measure incorrectly if the spherical sector produced from the ball bearing ball is not placed precisely polarly on the layer to be measured. With the probe already known in the art, the spherical sector has been welded to the topside of a plate of a threaded stem. During this welding, the spherical sector is heated and its permeability is changed in a nonreproducible manner. After welding, one may anneal both parts, so that a definite reproducible permeability can be achieved with this second operation. However, the spherical sector becomes mechanically soft and its wear resistance deteriorates.

The configuration of the known probe is such that, with the threaded stem screwed all the way into the magnetic core, the plate used for fastening the spherical sector makes contact with the magnetic core. Magnetically this means that the lines of force first pass through the spherical sector, then through the connecting layer between spherical sector and plate (which layer has magnetic leakage) and through the plate and only then to the front side of the core.

It is, therefore, an object of the present invention to create an arrangement where these disadvantages are avoided and which is less expensive to manufacture.

SUMMARY OF THE INVENTION

The objects of the present invention are achieved as follows:

a. The spherical sector projects with the edge of its plane surface beyond the front surface of the fastener.

b. The edge is in direct contact with the front surface of the carrier.

As a result it does not matter what magnetic properties the connecting layer between fastener and spherical sector has, because the lines of force may not leave the edge of the spherical sector and immediately enter the carrier.

The fastening element if made of soft magnetic material. The improvements result in a very good magnetic focusing of the lines of force throughout the coil. If the fastener were not soft-magnetic, one would have only 20 to 30 percent of the quality of the present invention.

The fastening element and the spherical sector are connected to one another by solder and wherein the crystalline structure of the spherical sector has been maintained the same as that of the ball bearing ball. The improvements result in a solid connection between fastener and spherical sector and maintenance of the original hardness of the ball bearing ball. This type of fastening is preferable to cementing (gluing) which would result in difficulties owing to the 2 to 3 square meter connection surfaces.

The carrier is a steel tube which is much longer than the fastening element and wherein the fastening element is a cylindrical pin which is coaxial with the spherical sector and with the steel tube and is interchangeably form and/or force locked therewithin. The improvements result in a possibility of simple stretching which makes it impossible that the soft-magnetic fastener, in spite of interchangeability exposed to excessive pressure. This pressure would result in a harmful effect similar to the of piezo-electricity.

The coil is cantilever-would and has a slightly larger inside diameter than the outside diameter of carrier plus the electrically insulating paint coat on the carrier. The improvements result in a repeating coil with perfect geometry. If this coil were wound directly onto the steel tube, one could prevent that, during the winding, the steel tube might not run coaxially and the coil design would be interfered with, if it were possible at all. In addition, it is possible to adjust the probe through the cantilever design by moving the coil axially along the steel tube.

The carrier on its side remote from the spherical sector is held by a coaxial non-magnetic carrier and is rigidly connected thereto, which latter carrier is connected to a base having at least three lead-in pins leading into it. The improvements result in a component combination which can be easily inserted into the jacket and sealed there. Furthermore, one may use the base to close the jacket from the rear. Such a design is particularly well-suited for very narrow pencil-like probes with which one may also measure the layers in holes.

The latter carrier is made of brass. The improvements result in a carrier which is unmagnetic and can easily be soldered.

The latter carrier has the shape of an axially symmetrical chalice whose stem is connected to the base and whose cup encloses the carrier. Due to the improvements, one can easily grasp the steel tube and the entire length of steel tube is available for the fastener.

The base is a socket for semiconductor components, is located coaxially with the carrier and wherein wires are soldered to its lead-in pins. The improvements result in a simple conventional precise base. With these bases the lead-in pins are embedded in glass beads which do not soften during soldering and provide good insulation.

The carrier, the coil, the latter carrier and the base are sealed coaxially in a jacket having one end closed stopper-like by the base and which has an outside diameter in the millimeter range. The improvements result in protection of the inside structure, an immovable geometry and a slender shape.

The jacket is made of non-magnetic metal and is spaced a distance from the coil so as to reduce its damping to a negligible amount. The improvements result in a jacket which meets all requirements. The jacket could be made from synthetic material. However, it has been found that with a sufficiently large spacing, the jacket can also be made of metal. In addition, this spacing simultaneously serves as a gap from which the sealing (pouring) material may penetrate beyond the coil to the forward end of the jacket. Otherwise, the hollow space in front of and behind the coil would have to be filled.

The jacket is joined to a grip jacket which houses a lead-in cable whose outside diameter is slightly smaller than the inside diameter of the grip jacket wherein the wires of the lead-in cable are connected to the lead-in pins on the base and wherein the grip jacket has peripheral grooves rolled into the lead-in cable. As a result of the improvements, the pressure with which the spherical sector may be pressed against the surface of a test object is automatically limited. This helps preserve the spherical sector and contributes to test results which are reproducible over long time intervals. Furthermore, it provides simple tension relief for the lead-in cables, requiring no additional space, and a simple connection between the lead-in pins and the cores of the cable.

A grip jacket is located in a limiter sleeve coaxial and movable therein, wherein the forward end of the probe projects from the limiter sleeve and can be displaced against the force of a spring beyond the forward front surface into the limiter sleeve. The improvements result in simple displaceability and limitation of the press-on force.

There is provided in one of the peripheral grooves a stop projecting beyond this peripheral groove on which stop rests one end of a coaxial spiral spring, wherein the other end of the spiral spring rests against a rear inside shoulder of the limiter sleeve and wherein the borehole ahead of the stop guides the circular probe with practically no play in the radial direction. The improvements result in double utilization of a peripheral bead for the limiter jacket, the space for the spiral spring and a simple and precise guidance.

The limiter sleeve comprises two partial sleeves which can be screwed to one another in the area of the stop. The improvements facilitate assembly. In particular, the stop and the spiral spring can be inserted and repaired easily.

The stop is also the stop for a shoulder of the limiter sleeve which it hits when it is moved back all the way. The improvements result in a simple impact for the maximum projection of the spherical sector.

The stop is a multipart ring. Due to the improvements the ring can be easily assembled in the peripheral bead (groove).

The ring has a coaxial flange pointing in the direction of the spiral spring around which flange one end of the spiral spring runs and holds the ring together. Due to the improvements, the spiral spring holds the ring together.

The novel features which are considered as characteristic for the invention are set forth in the following description of a preferred embodiment.

DESCRIPTION OF THE PREFERRED EMBODIMENT

Figure 1:
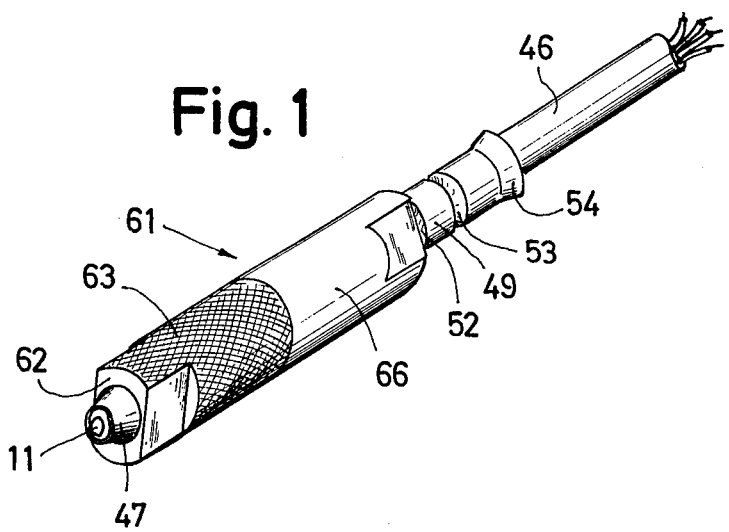
FIG. 1 is a perspective view of the probe with limiter jacket.

A hemisphere 11, perpendicular to its geometric longitudinal axis 12, has a plane surface 15 in the equatorial plane. Hemisphere 11 is made from a ball bearing ball of approx 2 mm diameter by grinding and has essentially the same crystal structure and the same hardness as the ball bearing ball. By means of a tin layer 13, a soft-magnetic pin 14 is soldered to the hemisphere with its upper front surface. Because of the difference in diameters, there remains an annular rim 16. Pin 14 is approx 4 mm long.

Figure 4:
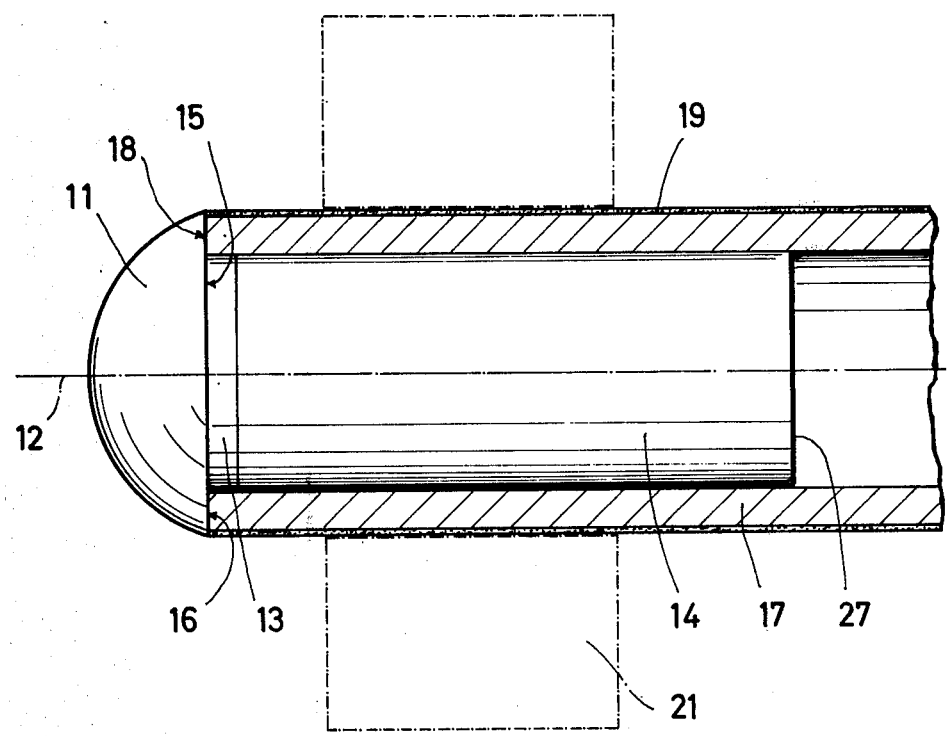
FIG. 4 is an enlarged side view of the spherical sector with fastener and carrier (indicated by broken lines).

An approx 5 mm long tube 17, made of V-2A steel, is located coaxially, has a diameter of 1.8 mm and an inside diameter of 1.62 mm. On its forward end, it has a front surface 18 cut-off at right angles to the longitudinal axis 12. As shown in FIG. 4, rim 16 projects a little beyond the front surface 18. Pin 14 can be placed into tube 17 and it will not fall out by itself. This prevention of drop-out can be achieved in various ways, without interfering with the geometric symmetry. For example, a sufficiently good grip is achieved if the diameter of pin 14 is made only slightly smaller than the inside diameter of tube 17. One may also slit the tube 17 and then squeeze it. One may also make a drill hole across pin 14, thread a perlon (german synthetic) thread through it and have it stick out on both sides, etc. On the outside of tube 17 which is a magnetizable carrier for the soft magnetic pin 14, soldered to the hemisphere is an electrically insulating paint coat 19. On tube 17, a repeating coil 21 is provided coaxially and with lengthwise displacement. The repeating coil is cantilever wound and has four connecting wires.

Figure 3:
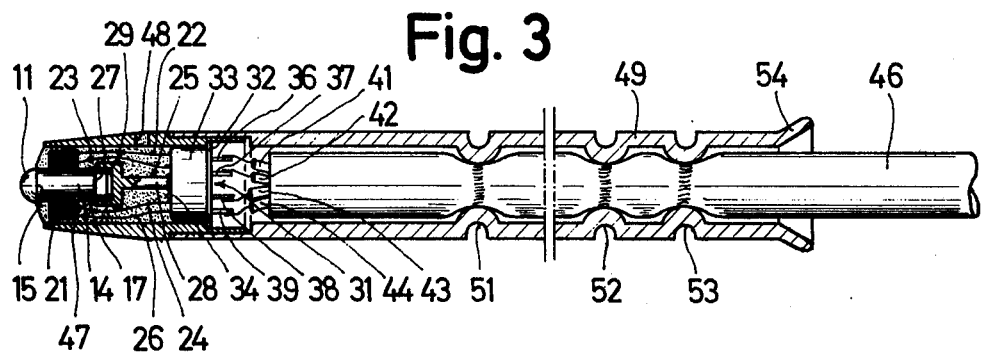
FIG. 3 shows the cut-open probe enlarged three times.

As shown in FIG. 3, there is an appreciable distance between the rear front surface 27 and the inside end of tube 17. There tin residue and dirt particles have enough room, if they are present.

A coaxial carrier 25 has a 3 mm long leg 28 to whose outer end a ring flange 29 is tip-stretched into which the right-hand end of tube 17, as shown in FIG. 3, can be soldered. The outside diameter of the ring flange 29 is 2.4 mm. The carrier 25 is made of brass. Its right end is soldered to a transistor socket 31. Such a transistor socket 31 contains iron and therefore had undesirable magnetic properties which may affect pin 14. For this reason, one provides a separation from the transistor socket 31 by means of carrier 25. This separation can also be brought about by making the tube 17 somewhat longer and connecting it to the transistor socket 31. However, the arrangement described causes fewer difficulties.

The transistor socket 31 has an annular rim 32, a cylindrical wall 33 which is coaxial and a bottom 34. Such transistor sockets are commercially available. They have electrical lead-in pins 36, 37, 38, 39 which pass through glass beads. Their left-hand ends are soldered to connecting wires 22, 23, 24, 26. Their right-hand ends are soldered to the cores 41, 42, 43, 44 of a cable 46.

A coaxial sleeve 47 has an inside diameter of 4.3 mm and therefore has a slightly larger diameter than the outside diameter of repeating coil 21. Its inside diameter corresponds to the outside diameter of wall 33 of transistor socket 31. Transistor socket 31, including carrier 25, tube 17 and repeating coil 21, is inserted coaxially from the rear into jacket 47 in the wired state. Rim 32 makes contact with a shoulder of jacket 47 and indicates the insertion depth, while wall 33 serves as centering guide. Jacket 47 projects only slightly on the left-hand side beyond repeating coil 21 and has a drill hole 48 in its wall. Through this hole, the sealing material can be injected (shown by dots in FIG. 3). It penetrates through the gap between the repeating coil 21 and jacket 47 toward the front. Since a spacer is used instead of pin 14 and hemisphere 11, the synthetic material cannot penetrate into tube 17. Nevertheless, according to FIG. 3 the jacket 47 is closed off in the front by synthetic material and the repeating coil 21 is protectively covered, even though it is located relatively far to the front.

If additional centering assistance is desired, one may provide a perforated disk which is made of nonmagnetic material and does not attenuate electrical fields. E.g., one may use a disk of synthetic material. This disk has an outside diameter in accordance with the inside diameter of jacket 47, and an inside diameter in accordance with the outside diameter of the tube 17. This disk is slid from the left-hand side onto the tube 17, makes contact in jacket 47 and thus centers the left-hand end of the assembly consisting of transistor socket 31, carrier 25, tube 17 and repeating coil 21.

With the configuration described, tube 17 has a thickness of approx 0.1 mm. This leads to a small eddy-current damping and a good coupling of the winding with the layer/carrier combination. The tube 17, of high-grade steel, has a low electrical conductivity and hence a low eddy-current damping. The arrangement is particularly well-suited for single-pole probes of very small diameter. Their diameters may be smaller than that of a conventional pencil.

Owing to the projection of rim 16 beyond pin 14, tolerances of many types can be eliminated. For example, the thickness and the area of the tin layer 13 do not play a part. Even when the hemisphere 11 is not seated entirely coaxially on pin 14, it does not matter as long as the front surface 18 makes contact on all sides with hemisphere 11, because the contact surface alone determines the transition of the lines of force. Calibration of the system is very simple. One takes a calibration standard of known layer thickness, places the hemisphere 11 on it and moves the cantilever-wound repeating coil until the measuring instrument indicates the correct value.

Figure 2:
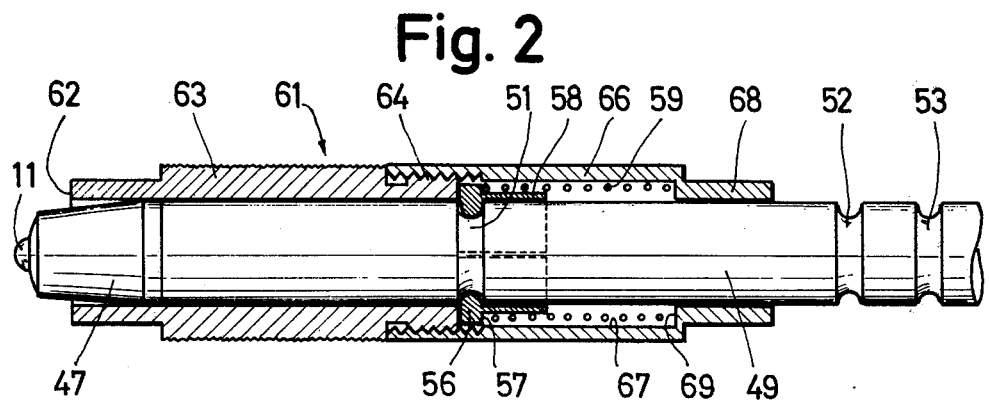
FIG. 2 is a side view of the probe with the limiter jacket cut open.

On the right-hand side, according to FIGS. 2 and 3, jacket 47 joins a grip jacket 49, also made of brass, which has the same outside diameter as the maximum outside diameter of jacket 47, hence is practically flush with it, and which extends over the turned right-hand rim of the jacket 47. In the embodiment shown, the grip jacket 49 is approx 50 mm long. In its periphery there are three grooves 51, 52, 53 to such an extent that they jam the jacket of cable 46 and result in effective tension relief for the soldering between cores 41, 42, 43, 44 and the lead-in pins 36, 37, 38, 39. To prevent bending, a flare 54 is provided on the right-hand side of grip jacket 49.

The groove 51 is also used to provide a seat for a two-part ring 56 which extends into the groove 51 and projects with a shoulder 57 beyond the grip jacket 49. Also, a coaxial flange 58 is tip-stretched at ring 56 pointing to the right. A spiral spring 59 is slid with its left-hand end onto this flange 58 and contacting shoulder 57, thus holding the multi-part ring together.

As shown in FIGS. 1 and 2 limiter sleeve (jacket) is located coaxially. Without exerting any forces, its left-hand rim 62 is considerably behind the hemisphere 11. As is best seen from FIG. 2 the left-hand half 63 of limiter sleeve 61 has an inside diameter slightly larger that the outside diameter of grip jacket 49 so that it guides the grip jacket 49 coaxially. Its right-hand end has an outside thread 64. The right-hand half 66 of limiter sleeve 61 has an inside thread on the left-hand side which is threaded onto the outside thread 64; its bore 67 extends over ring 56 and over spiral spring 59. The bore 67 is much longer than flange 58. On the right-hand side, part 66 has a tip-stretched sleeve 68 which has a slightly larger diameter than grip jacket 49 and can slide on it coaxially. This results in an inside shoulder 69 on which the right-hand end of spiral spring 59 rests.

The limiter sleeve 61 slides to the left and thus relieves the hemisphere 11 if the probe is placed with excessive pressure. Hence, the hemisphere 11 is always applied with the same force, while rim 62 takes the excess force.

Of course, limiter sleeve 61 increases the diameter of the arrangement. If one wishes to measure in narrow boreholes, grooves, corners, etc., it is advisable to leave it out and to hold the probe like a pencil in grip jacket 49. Assembly and disassembly of limiter sleeve 61 is extremely simple since it has few parts and cannot be assembled the wrong way.

What is claimed is:
1. A probe having a soft magnetic pole piece and a magnetizable carrier, for measuring the thickness of thin non-ferromagnetic layers on a ferromagnetic base by substantially detecting the reluctance of said thin layers between said base and said pole piece, said pole piece comprising a spherical sector comprised of a ball bearing ball having a flat side provided by grinding and an elongated fastening element connected to the ground side of said spherical sector and being interchangeably fastened to said magnetizable carrier, said magnetizable carrier carrying transmission coil means for generating an a.c. magnetic field penetrating through the non-ferromagnetic layer and into the ferromagnetic base therebelow and for generating an electric response signal depending on the thickness of said thin non-ferromagnetic layer, wherein,
a. said fastening element is a cylindrical pin having a flat end surface, which is coaxial with said spherical sector and connected thereto by solder between the ground side of said spherical sector and said flat end surface of said pin, the crystalline structure of said spherical sector being substantially maintained the same as that of the original ball bearing ball, a rim portion of the ground side of said spherical sector projecting beyond the end surface of said cylindrical pin,
b. said carrier is a thin-walled steel tube coaxially surrounding said cylindrical fastening element and abutting with its complete ring-shaped end surface against said rim portion of the ground side of said spherical sector, and
c. said steel tube is interchangeably force-and/or formlocked to said cylindrical fastening element and is considerably longer than said cylindrical fastening element.

2. The probe according to claim 1 wherein said steel tube on its end remote from the spherical sector is held by an electrically conductive but nonmagnetic carrier coaxially arranged with the tube and rigidly connected thereto, which carrier is adapted to be rigidly connected to a base arranged at a distance from said steel tube and having at least three contact pins electrically connected to said transmission-coil means for inputting an a.c. electromagnetic field to the layer-base arrangement and for outputting the response signal from the transmission-coil means.

3. The probe according to claim 1 wherein the coil is cantilever-wound and has a slightly larger inside diameter than the outside diameter of carrier plus the electrically insulating paint coat on the carrier.

4. The probe according to claim 2, wherein the latter carrier is made of brass.

5. The probe according to claim 2 wherein the latter carrier has the shape of an axially symmetrical chalice whose stem is connected to the base and whose cup encloses the carrier.

6. The probe according to claim 2 wherein the base is a socket for semiconductor components, is located coaxially with the carrier and wherein wires are soldered to its lead-in pins.

7. The probe according to claim 2 wherein the carrier, the coil, the latter carrier and the base are sealed coaxially in a jacket having one end closed stopper-like by the base and which has an outside diameter in the millimeter range.

8. The probe according to claim 7 wherein the jacket is made of nonmagnetic metal and is spaced a distance from the coil so as to reduce its damping to a negligible amount.

9. The probe according to claim 7 wherein the jacket is joined to a grip jacket which houses a lead-in cable whose outside diameter is slightly smaller than the inside diameter of the grip jacket wherein the wires of the lead-in cable are connected to the lead-in pins on the base and wherein the grip jacket has peripheral grooves rolled into the lead-in cable.

10. The probe according to claim 9 wherein a grip jacket is located in a limiter sleeve coaxial and movable therein, wherein the forward end of the probe projects from the limiter sleeve and can be displaced against the force of a spring beyond the forward front surface into the limiter sleeve.

11. The probe according to claim 10 wherein there is provided in one of the peripheral grooves a stop projecting beyond this peripheral groove on which stop rests one end of a coaxial spiral spring, wherein the other end of the spiral spring rests against a rear inside shoulder of the limiter sleeve and wherein the borehole ahead of the stop guides the circular probe with practically no play in the radial direction.

12. The probe according to claim 11 wherein the limiter sleeve comprises two partial sleeves which can be screwed to one another in the area of the stop.

13. The probe according to claim 11 wherein the stop is also the stop for a shoulder of the limiter sleeve which it hits when it is moved back all the way.

14. The probe according to claim 11 wherein the stop is a multipart ring.

15. The probe according to claim 14 wherein the ring has a coaxial flange pointing in the direction of the spiral spring around which flange one end of the spiral spring runs and holds the ring together.

16. The probe according to claim 1 wherein the fastening element and the spherical sector are connected to one another by a welded joint.

* * * * *